(12) United States Patent
Bulumulla et al.

(10) Patent No.: US 7,173,426 B1
(45) Date of Patent: Feb. 6, 2007

(54) OPTICAL LINK FOR TRANSMITTING DATA THROUGH AIR FROM A PLURALITY OF RECEIVER COILS IN A MAGNETIC RESONANCE IMAGING SYSTEM

(75) Inventors: Selaka Bandara Bulumulla, Niskayuna, NY (US); Glenn Alan Forman, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/288,555

(22) Filed: Nov. 29, 2005

(51) Int. Cl.
*G01V 3/00* (2006.01)

(52) U.S. Cl. ........................ 324/318; 324/322

(58) Field of Classification Search ............... 324/322, 324/318, 319, 309, 307, 306, 300; 600/410–424; 359/172, 152–154, 189, 184, 159; 318/128–131
See application file for complete search history.

(56) References Cited

U.S. PATENT DOCUMENTS

| | | | |
|---|---|---|---|
| 3,150,313 A * | 9/1964 | Dehmelt | 324/304 |
| 4,777,438 A * | 10/1988 | Holland | 324/309 |
| 4,825,162 A * | 4/1989 | Roemer et al. | 324/318 |
| 5,359,446 A | 10/1994 | Johnson et al. | |
| 5,978,438 A * | 11/1999 | Resnick et al. | 378/4 |
| 6,108,483 A | 8/2000 | Berkcan | |
| 6,122,084 A * | 9/2000 | Britz et al. | 398/131 |
| 6,154,299 A | 11/2000 | Gilbreath et al. | |
| 6,335,811 B1 * | 1/2002 | Sakanaka | 398/129 |
| 6,396,613 B1 | 5/2002 | Harrison et al. | |
| 6,507,683 B2 | 1/2003 | Sugitatsu et al. | |
| 6,522,437 B2 * | 2/2003 | Presley et al. | 398/128 |
| 6,563,106 B1 | 5/2003 | Bowers et al. | |
| 6,856,437 B2 | 2/2005 | Witt et al. | |
| 7,035,546 B2 * | 4/2006 | Keller et al. | 398/131 |
| 7,054,563 B2 * | 5/2006 | Tsumura | 398/169 |
| 2004/0019273 A1 | 1/2004 | Helfer et al. | |
| 2004/0030233 A1 | 2/2004 | Frazier et al. | |
| 2004/0076390 A1 * | 4/2004 | Dong Yang et al. | 385/116 |
| 2006/0139029 A1 * | 6/2006 | Abbink et al. | 324/318 |

OTHER PUBLICATIONS

Jayasri Akella, Chang Liu, David Partyka, Murat Yuksel, Shivkumar Kalyanaraman, and Partha Dutta, "Building Blocks for Mobile Free-space-Optical Networks", Research Paper downloaded from ww.ecse.rpi.edu/Homepages/shivkuma/research/papers/winet05.pdf.

E. M. Strzelecka, et al., "Parallel free-space optical interconnect based on arrays of vertical-cavity lasers and detectors with monolithic microlenses", *Applied Optics*, vol. 37, No. 14, May 1998, pp. 2811-2821.

G.C. Gilbreath, et al., "Large-aperture multiple quantum well modulating retroreflector for free-space optical data transfer on unmanned aerial vehicles", *Optical Engineering*, 40(7) Jul. 2001, pp. 1348-1356.

* cited by examiner

*Primary Examiner*—Brij B. Shrivastav
(74) *Attorney, Agent, or Firm*—Jean K. Testa; Donald S. Ingraham

(57) ABSTRACT

An optical data link is provided for optically transmitting in free space data from a plurality of receiver coils in a magnetic resonance (MR) imaging system. This free space (e.g., through-the-air) optical data link provides a tether-less (i.e., no bundles of physical wires or optic fibers), essentially electro-magnetically immune (no interference as in radio-frequency wireless transmissions) and scalable solution to transmit data usable to create an MR image.

22 Claims, 4 Drawing Sheets

OPTICAL LINK FOR TRANSMITTING DATA THROUGH AIR FROM A PLURALITY OF RECEIVER COILS IN A MAGNETIC RESONANCE IMAGING SYSTEM

FIELD OF THE INVENTION

The present invention is generally related to magnetic resonance imaging, and more particularly, to an optical data link for optically transmitting in free space data from a plurality of receiver coils in a magnetic resonance imaging system.

BACKGROUND OF THE INVENTION

In a magnetic resonance imaging (MRI) system, there may be multiple, highly sensitive receiver coils, e.g., surface coils. As is known in the art, these coils are generally used as antennae to receive MR response signals for a region of a subject undergoing a diagnostics MR procedure to create an MR image of that region. For example, presently there may be eight or sixteen receiver coils in a typical MRI system. It is noted, however, that this number may eventually increase to a larger number, (e.g., 32, 64, 128 coils or more) as newer MRI systems with ever-increasing imaging resolution are introduced in the market place.

As the number of receiver coils grows, providing effective electrical connections through a bundle of cables, e.g., coaxial cables, between these coils and a receiver become problematic. For example, a large number of cables could pose a hazardous condition in the high magnetic field environment of the MR system. In addition, a large number of cables incrementally add to the footprint and weight taken by the coil signal receiver. Moreover, since the receiver coils may be placed on the patient, additional weight due to physical interconnects is undesirable.

Some known techniques have attempted to address the foregoing difficulties through the use of fiber optic cables, or wireless radio-frequency transmissions for communicating the signals sensed by the receiver coils. With fiber optic cables, the hazards that may be posed by coaxial cables when subjected to magnetic fields are significantly reduced or eliminated. However, a cost-effective scalable solution suitable for high-resolution MRI applications remains an issue since the number of fiber optic connections increases as a direct function of the number of receiver coils used by the MRI system. In the case of wireless radio-frequency transmissions, this type of link may entail burdensome approval procedures involving regulatory agencies that regulate the allocation and utilization of radio spectral frequencies. In addition, this type of link may generate undesirable electromagnetic interference at the highly sensitive receiver front end. Also, wireless transmitters may require a relatively high amount of power to operate.

Accordingly, it is desirable to provide an MRI system and techniques that avoid or substantially reduce the above-described difficulties, such as may be achieved with a through-the-air (e.g., tetherless) optical data link that eliminates the need for physical cables and provides a scalable and cost-effective solution that can be readily adapted, particularly when the MRI system uses a large number of receiver coils.

BRIEF DESCRIPTION OF THE DRAWINGS

These and other advantages of the invention will be more apparent from the following description in view of the drawings that show.

DETAILED DESCRIPTION OF THE INVENTION

Figure 1:
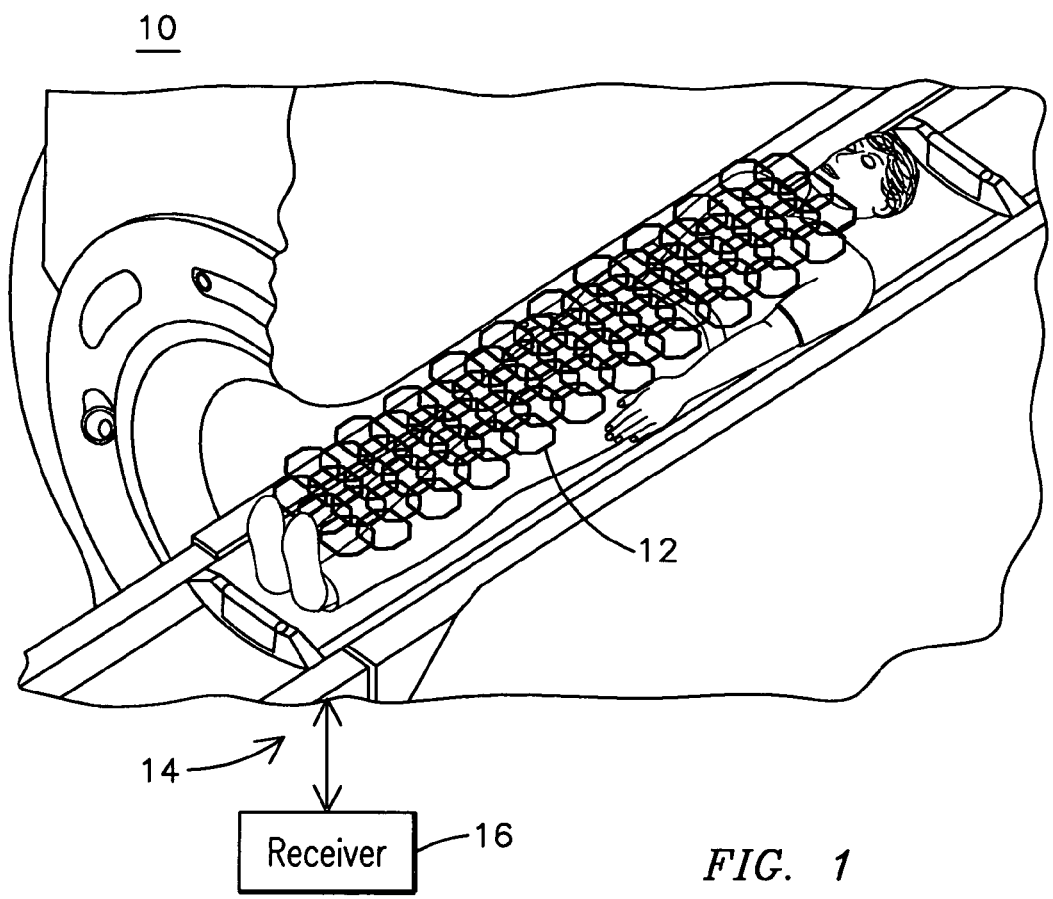
FIG. 1 is a cut-away, perspective view of a magnetic resonance imaging (MRI) system embodying aspects of the present invention.

FIG. 1 illustrates a cut-away, perspective view of a magnetic resonance imaging (MRI) system 10 embodying aspects of the present invention. MRI system 10 comprises a plurality of receiver coils, e.g., surface coils 12, as may be positioned on a subject undergoing an MRI diagnostics scan. Each receiver coil is configured to supply a respective coil output signal based on a magnetic resonance response signal sensed by the receiver coil. Using techniques well understood by those skilled in the art, each of the coil signals is digitized and processed to create an MR image of a region of interest.

The inventors of the present invention have recognized an innovative optical data link 14 that may be configured to transmit digitized data from the receiver coils 12 to a remote optical receiver 16. This free space (e.g., through-the-air) optical data link provides a tether-less (i.e., no bundles of physical wires or optic fibers), electro-magnetically immune (no interference as in radio-frequency wireless transmissions) and scalable solution to transmit data usable to create the MR image.

Figure 2:
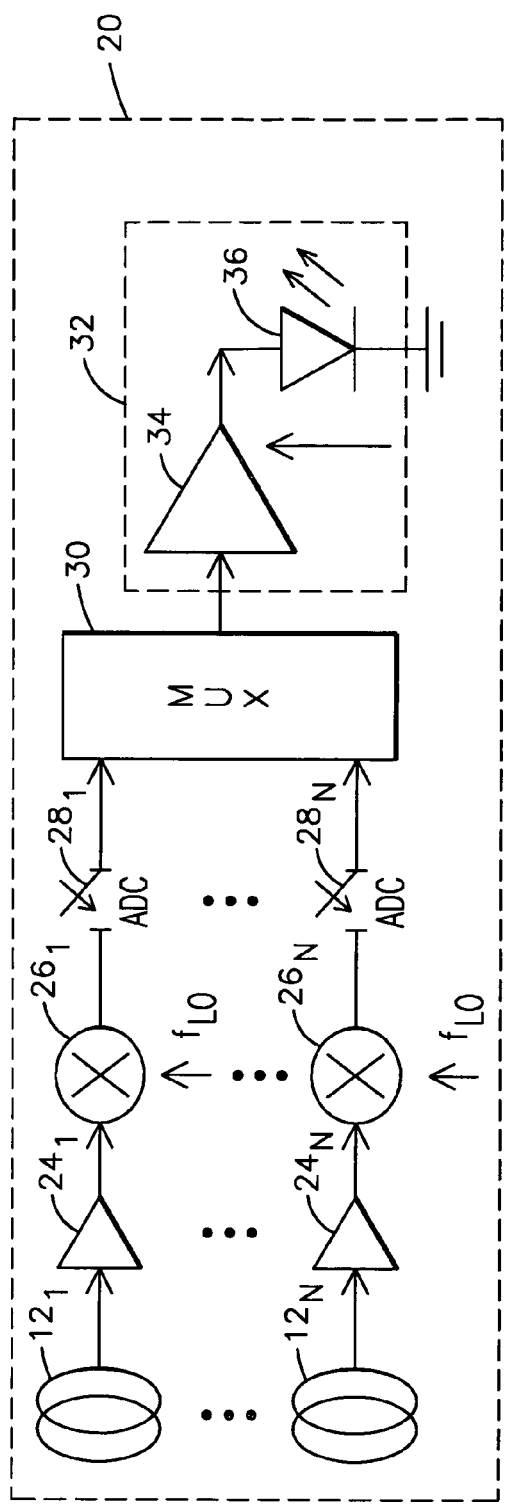
FIG. 2 is a block diagram schematic of one exemplary transmitter circuitry, as may be configured for carrying a directed optical transmission.

It is contemplated that in one exemplary embodiment that uses a directed optical transmission, a transmitter circuitry 20 may be co-packaged with the receiver coils $12_1$–$12_n$ as shown in FIG. 2. For example, each signal from a receiver coil 12 may be amplified by a pre-amplifier 24, down-converted in frequency by a frequency converter 26, digitized by an analog-to-digital converter 28, multiplexed by a multiplexer 30 and connected to an optical source 32 that may be co-packaged with the receiver coils and the transmitter circuitry.

It will be appreciated that the amplified signal may also be digitized directly, without down-conversion in frequency (e.g., direct sampling). The optical source 32, such as may comprise an optical source driver 34 and a light source 36, is controlled by the transmit circuitry, and enables to optically transmit the receiver coil data over free space. The light source may be a light emitting diode (LED) source, or a laser source (e.g. Vertical Cavity Surface Emitting Laser (VCSEL), Distributed Feedback Laser (DFB) or Fabry-Perot laser). FIG. 2 depicts one exemplary embodiment where signals from multiple receiver coils may be multiplexed to a single, high speed, optical source. It is contemplated that this implementation may require an incremental consumption of electrical power at the receiver coil circuit for powering the transmitter circuit and optical source.

In order to receive this optical transmission, one or more receivers 16 (FIG. 1) may be positioned at any of various locations, such as inside the magnet bore. In this case, the optical path would be relatively short (e.g., in the order of about one foot). However, this could subject the receiver components to the relatively high magnetic fields that are formed at or near the imaging volume. In another example, one or more receivers 16 may be positioned at the ceiling of the room where the MRI system is located. In this case, the transmission distance would be relatively longer as compared to the preceding example. However, the receiver components would be farther away from the imaging volume. In yet another example, a passive reflective surface or other reflective elements may be disposed on the magnet bore surface to reflect the optical signal to one or more receivers outside the imaging volume.

To maintain a reliable optical data link, alignment between the optical transmitter and receiver should be maintained to a relatively high degree of accuracy. However, this alignment may be affected since the transmitter may move due to patient movement during the scan.

Figure 3:
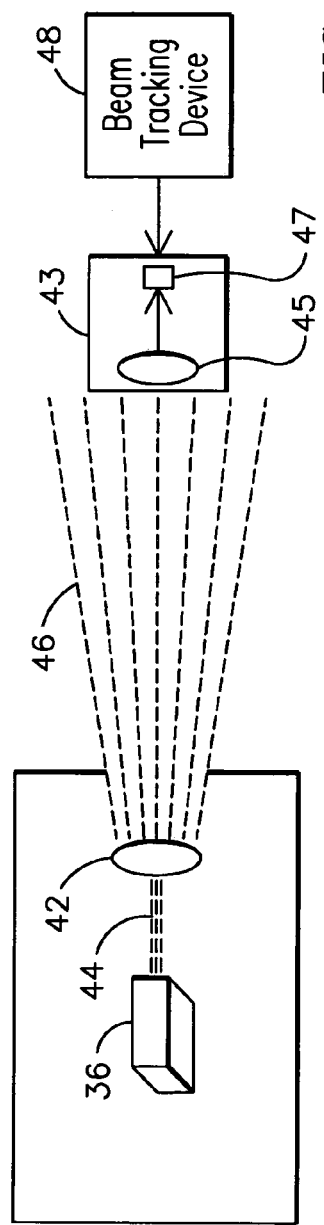
FIG. 3 is a block diagram of an exemplary transmitter including an optical lens arrangement that may be used for spatially expanding a transmitted optical beam.

In one exemplary embodiment shown in FIG. 3, an optically divergent lens 42 may be positioned to receive the laser beam 44 from the laser source 36 so that the transmitted beam 46 can be spatially expanded. In this embodiment, a receiver 43 including a light collecting lens 45 and light detector 47 may be configured with beam tracking capability, such as may be provided by a beam tracking device 48 configured to track, for example, transmitter movement.

Figure 4:
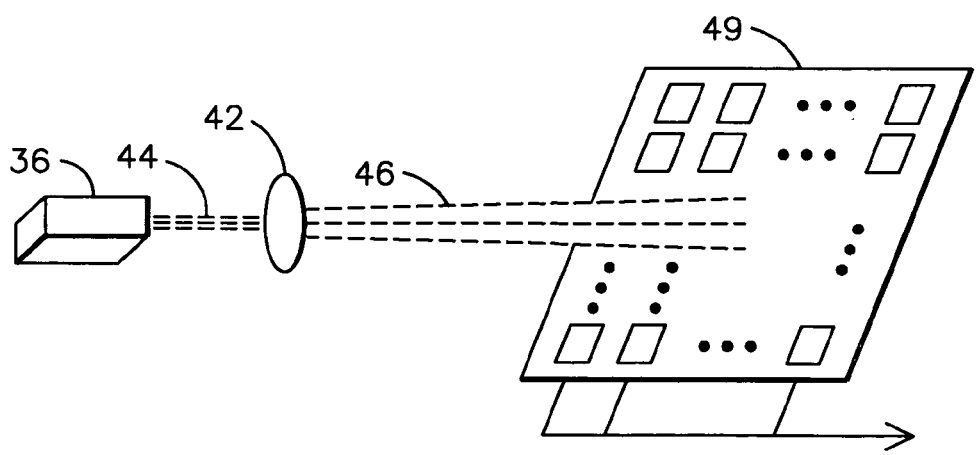
FIG. 4 is a block diagram of an exemplary embodiment that provides an array of optical receivers that may be used to acquire the transmitted beam.

In one alternative exemplary embodiment shown in FIG. 4, an array 49 of optical receivers may be used to acquire the transmitted beam. For example, due to the relatively larger surface area of the receiver array as compared to a single receiving element, at least one or more of the receivers is likely to be exposed to the transmitted beam, even during movement by the patient. Array 49 may be a two dimensional array made of a flexible material, such as Kapton polyimide or any suitable polymer. A processor configured to decide on the data transmitted from the optical source may be used to process the signals supplied by the array of receivers.

Figure 7:
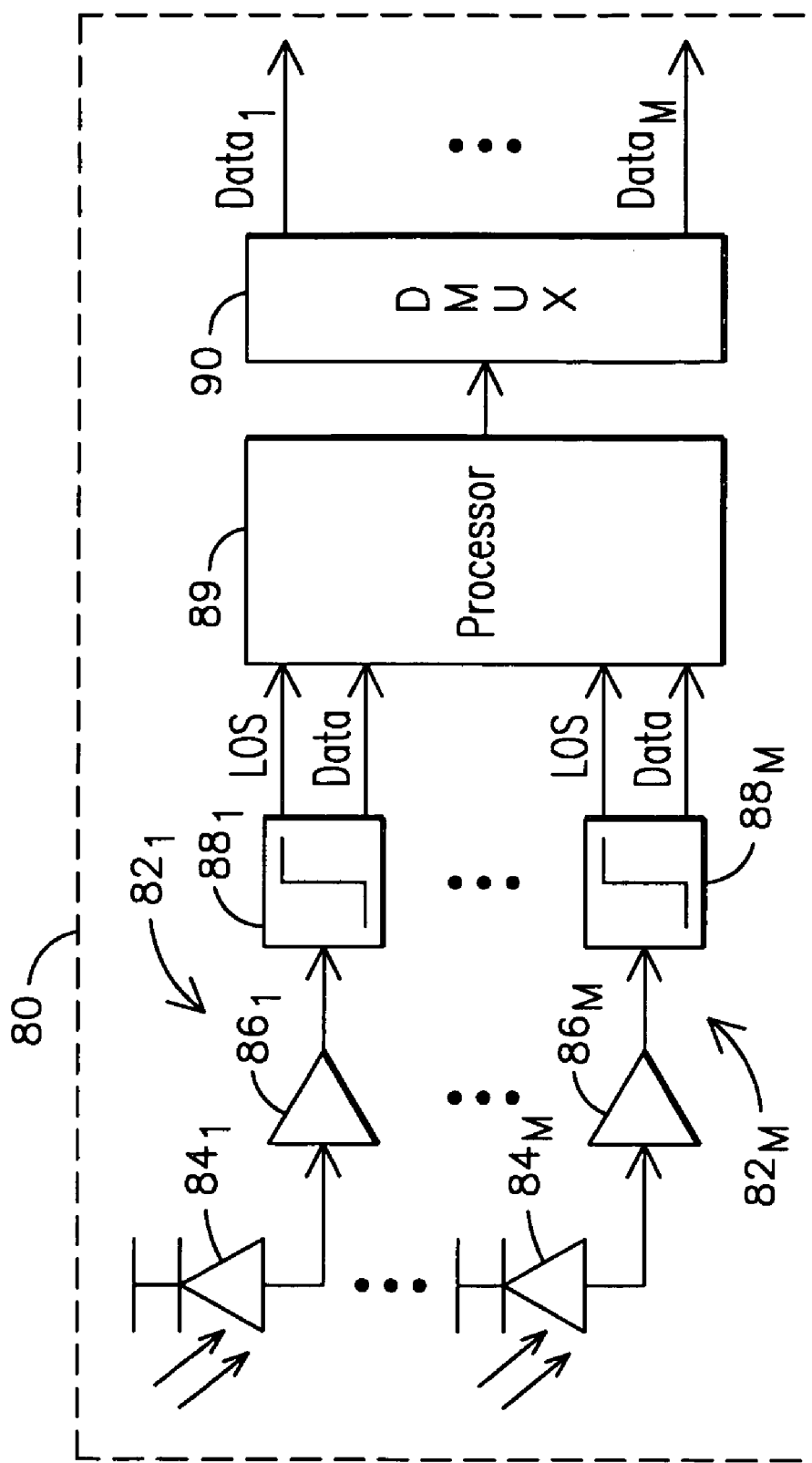
FIG. 7 is a block diagram schematic of exemplary receiver circuitry as may be configured to acquire receiver coil data with an array of optical detectors.

FIG. 7 illustrates a block diagram of an exemplary receiver circuitry 80 that comprises an array of receivers 82. For example, each respective signal from a photodiode detector 84 may be amplified by an amplifier 86 (e.g., trans-impedance amplifier), may be limited by a limiting amplifier 88 that can additionally provide loss of signal (LOS) information, may be processed by a processor 89 configured to decide on the array data to be demultiplexed by a demultiplexer 90 connected to an imaging processor, (not shown) configured to generate an image using techniques well understood by those skilled in the art.

Figure 5:
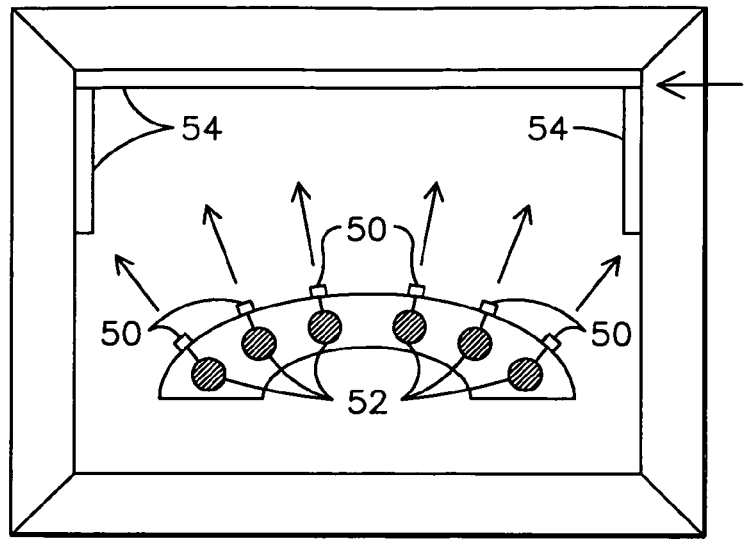
FIG. 5 is a schematic representation of another exemplary embodiment of an optical data link that includes an optical source directly integrated with the receiver coil to transmit a light beam optically modulated to carry receiver coil signal information through the air.

In another exemplary embodiment illustrated in FIG. 5, an optical transmitter 50 is integrated with a respective receiver coil 52. That is, the transmitter, in lieu of being used to transmit a multiplexed data stream from all of the receiver coils, may be used to transmit data from only one receiver coil (i.e. each receiver coil has an optical transmitter). In this embodiment, each light source located at the receiver coil circuit is directly responsive to digitized coil output data to optically modulate the optical beam to be transmitted through air to one or more spaced apart optical detectors 54.

It will be appreciated that one exemplary technique for effecting the optical transmission may be a directed (line-of-sight) transmission wherein an optical transmitter and a corresponding optical receiver establish an optical link by way of a singular optical path (line-of-sight path). For example, this technique may require a specified spatial alignment between the transmitter and the receiver. It will be appreciated that if the spot size for the transmitted beam is relatively large, then the alignment requirements would be less demanding. For example, assuming Infrared Data Association (IrDA) standards, the spot size may be 50 cm at 1 m away and, in this example, having to provide alignment at a micron level would not be necessary. This may be further alleviated by the use of a receiver array, as mentioned before.

It is contemplated that with relatively large spot sizes, multiple optical transmissions are likely to overlap and in this case one may need to encode the transmissions using a suitable encoding scheme (e.g. orthogonal coding, spread spectrum, etc.) to reduce effects of interference due to such overlapping, as would be well understood in the art of multi-user communication systems. It will be appreciated that many different techniques may be used to mitigate the effect of interference, such as Direct-Sequence (DS) spread spectrum.

Figure 6:
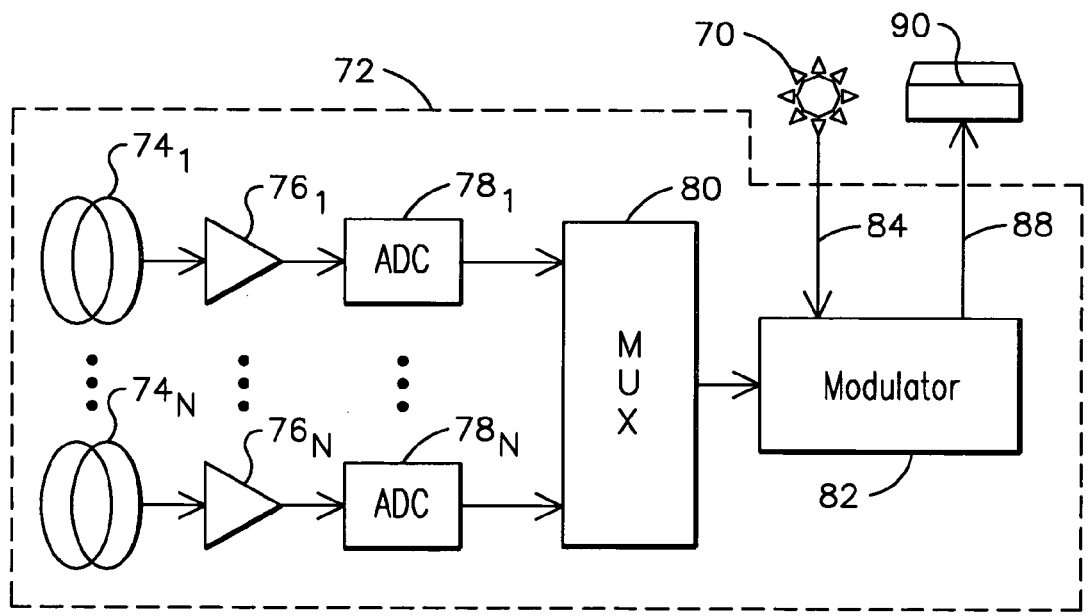
FIG. 6 is a schematic representation of one exemplary embodiment of an optical data link that includes a remote optical source with respect to a receiver coil to provide a light beam to be optically modulated with modulating circuitry integrated with the receiver coil to carry receiver coil signal information through the air.

In one exemplary embodiment illustrated in FIG. 6, an optical light source 70 is disposed spaced apart from a receiver coil circuit 72 that may include one or more receiver coils 74, one or more pre-amps 76, one or more analog-to-digital (A/D) converters 78, a data multiplexer 80 and an optical modulator 82. Optical light source 70 may be a light-emitting diode (LED), or laser (e.g., VCSEL, DFB or Fabry-Perot). In operation, a light beam 84 is directed from the remote optical source 70 towards optical modulator 82 that may be integrated with the receiver coil(s) 74 to receive the signal supplied by the multiplexer 80 to generate a modulated optical signal 88 to be received by an optical detector 90, such as a photodiode. For example, the photodiode may be a PIN type or avalanche photo-diode type. Detector 90 is spaced apart from the receiver coil circuit 72 and may be configured to operate as a direct detection receiver. It is expected that this embodiment may enable relatively low power dissipation at the receiver coil circuit 72, as the remote optical source 70 is not part of such a circuit.

By way of example, the optical modulator 82 may take the form of a Micro-Electro-Mechanical Systems (MEMS) mirror (e.g., an optical modulating switch configured to provide intensity modulation). For example, the MEMS mirror may be set in a first modulating state to reflect the light beam 84 and thereby generate a digital "one" and may be set in a second modulating state to not reflect the light beam and thereby generate a digital "zero". In another example, the optical modulator 82 may take the form of a retro-reflective modulator configurable in a first modulating state to reflect the light beam 84 and thereby generate a digital "one" and further configurable in a second modulating state to absorb the incident light beam and thereby generate a digital "zero". For readers desirous of additional background information in connection with retro-reflective modulators, reference is made to U.S. Pat. No. 6,154,299 that describes an example of a modulating retro-reflector that uses multiple quantum well technology.

The optical light source 70 may be configured to operate at relatively long wavelengths (e.g. in the order of approximately 1550 nm) since light at these longer wavelengths tends to be absorbed by the human cornea and associated lens, and is not focused on the retina. Thus, longer wavelength transmissions can enable relatively higher powers, (e.g., in the order of 10 mW for point sources) while maintaining eye safety. It will be appreciated that the present invention is not limited to the foregoing light wavelength being that this is just one example and other wavelengths may be used, provided the power levels are appropriately adjusted to meet any applicable eye safety standards. Thus, in general, light from the optical source may be selected to have a wavelength and/or power level appropriate to limit adverse effects to human eyesight.

Another exemplary technique for effecting the optical transmission may be a non-directed transmission, such as a diffuse optical transmission wherein the optical signal would be reflected from objects, walls, etc, to be eventually collected at the receiver. In this case, the concept of establishing a singular line-of-sight path is not applicable.

Exemplary Data Rate Requirements

Assuming that for each receiver coil, the signal is centered at 64 MHz, and with a maximum bandwidth of 1 MHz Further assuming that the receiver coil signal is sampled at a rate of 2 MSPS, and converted from analog-to-digital form to provide 16 bits of information Then each receiver coil would generate 16×2 Mb/s data or serial 32 Mb/s data Since the total data rate for MRI scales up with the total number of receiver coils in the system, (e.g., with a system that uses 128 coils) the aggregate data rate would be approximately 128×32 Mb/s=4.096 Gb/s)

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

We claim:

1. A magnetic resonance (MR) imaging system comprising:
   a plurality of receiver coils configured to supply respective coil output signals based on a plurality of magnetic resonance response signals sensed by the receiver coils; and
   an optical link coupled to the plurality of receiver coils to transmit through air at least one optical beam configured to carry receiver coil signal information; wherein said optical link comprises at least one receiver coil circuit comprising an analog-to-digital converter electrically coupled to a receiver coil to supply a digitized coil signal, wherein the receiver coil circuit further comprises an optical modulator responsive to the digitized coil signal to generate a modulator output signal, wherein said modulator output signal constitutes an optical beam transmitted though air and configured to carry the coil signal information.

2. The magnetic resonance (MR) imaging system of claim 1 wherein said optical link further comprises an optical source spaced apart from said receiver coil circuit, said optical source positioned to transmit through air an optical beam to be modulated by said optical modulator in response to said digitized coil signal.

3. The magnetic resonance (MR) imaging system of claim 1 wherein said optical modulator comprises a Micro-Electro-Mechanical Systems (MEMS) mirror.

4. The magnetic resonance (MR) imaging system of claim 1 wherein said optical modulator comprises a modulating retro-reflector.

5. The magnetic resonance (MR) imaging system of claim 1 wherein said optical link further comprises at least one optical detector spaced apart from the receiver coil circuit and positioned to receive the modulator output signal transmitted through air.

6. The magnetic resonance (MR) imaging system of claim 2 wherein light from the optical source comprises a wavelength and/or power level selected to limit effects to human eyesight.

7. The magnetic resonance (MR) imaging system of claim 1 wherein said optical link comprises at least one receiver coil circuit comprising an analog-to-digital converter electrically coupled to a receiver coil to supply a digitized coil signal, wherein the receiver coil circuit further comprises at least one optical source disposed at said receiver coil circuit, said optical source positioned to transmit through air an optical beam modulated in response to the digitized coil signal, wherein the optical beam transmitted by the optical source constitutes an optical beam configured to carry the coil signal information.

8. The magnetic resonance (MR) imaging system of claim 7 wherein said optical link further comprises at least one optical detector spaced apart from the receiver coil circuit and positioned to receive the optical beam transmitted by the optical source through air.

9. The magnetic resonance (MR) imaging system of claim 3 wherein said optical link comprises a receiver coil circuit comprising a plurality of analog-to-digital converters respectively coupled to a plurality of receiver coils to supply a plurality of digitized coil signals, wherein the receiver coil circuit further comprises a multiplexer connected to pass the plurality of digitized coil signals to an optical modulator to generate a modulator output signal, wherein said modulator output signal constitutes an optical beam transmitted though air and configured to carry the coil signal information from each of the plurality of receiver coils.

10. The magnetic resonance (MR) imaging system of claim 3 wherein said optical link comprises at least one receiver coil circuit comprising an analog-to-digital converter electrically coupled to a receiver coil to supply a digitized coil signal, wherein the receiver coil circuit further comprises at least one optical source disposed at said receiver coil circuit, said optical source configured to transmit an optical beam modulated in response to the digitized coil signal, said optical link further comprising lens optics optically coupled to the optical source and configured to spatially expand the optical beam transmitted by the optical source.

11. The magnetic resonance (MR) imaging system of claim 7 wherein said optical link further comprises an optical detector spaced apart from the receiver coil circuit and positioned to receive the optical beam transmitted by the optical source through air, said optical detector comprising a two-dimensional array of receivers configured so that at least one or more of the receivers In the array receive the optical beam notwithstanding of movement of the optical source due to patient motion.

12. An optical link for a magnetic resonance (MR) imaging system comprising a plurality of receiver coils configured to supply respective coil output signals based on a plurality of magnetic resonance response signals sensed by the receiver coils, said optical link comprising at least one receiver coil circuit coupled to the plurality of receiver coils to transmit through air a plurality of optical beams configured to carry coil signal information, wherein said receiver coil circuit comprises an analog-to-digital converter electrically coupled to a receiver coil to supply a digitized coil signal, wherein the receiver coil circuit further comprises an optical modulator responsive to the digitized coil signal to generate a modulator output signal, wherein said modulator output signal constitutes an optical beam transmitted though air and configured to carry the coil signal information.

13. The optical link of claim 12 further comprising an optical source spaced apart from said receiver coil circuit, said optical source positioned to transmit through air an optical beam to be modulated by said optical modulator in response to said digitized coil signal.

14. The optical link of claim 12 wherein said optical modulator comprises a Micro-Electro-Mechanical Systems (MEMS) mirror.

15. The optical link of claim 12 wherein said optical modulator comprises a modulating retro-reflector.

16. The optical link of claim 12 further comprising at least one optical detector spaced apart from the receiver coil circuit and positioned to receive the modulator output signal transmitted through air.

17. The optical link of claim 12 wherein light from the optical source comprises a wavelength and/or power level selected to limit effects to human eyesight.

18. The optical link of claim 12 wherein the receiver coil circuit comprises an analog-to-digital converter electrically coupled to a receiver coil to supply a digitized coil signal, wherein the receiver coil circuit further comprises at least one optical source disposed at said receiver coil circuit, said optical source positioned to transmit through air an optical beam modulated in response to the digitized coil signal, wherein the optical beam transmitted by the optical source constitutes an optical beam configured to carry said coil signal information.

19. The optical link of claim 18 further comprising at least one optical detector spaced apart from the receiver coil circuit and positioned to receive the optical beam transmitted by the optical source through air.

20. The optical link of claim 12 further comprising a receiver coil circuit comprising a plurality of analog-to-digital converters respectively coupled to a plurality of receiver coils to supply a plurality of digitized coil signals, wherein the receiver coil circuit further comprises a multiplexer connected to pass the plurality of digitized coil signals to an optical modulator to generate a modulator output signal, wherein said modulator output signal constitutes an optical beam transmitted though air and configured to carry the coil signal information from each of the plurality of receiver coils.

21. The optical link of claim 12 further comprising at least one receiver coil circuit comprising an analog-to-digital converter electrically coupled to a receiver coil to supply a digitized coil signal, wherein the receiver coil circuit further comprises at least one optical source disposed at said receiver coil circuit, said optical source configured to transmit an optical beam modulated in response to the digitized coil signal, said optical link further comprising lens optics optically coupled to the optical source and configured to spatially expand the optical beam transmitted by the optical source.

22. The optical link of claim 18 further comprising an optical detector spaced apart from the receiver coil circuit and positioned to receive the optical beam transmitted by the optical source through air, said optical detector comprising a two-dimensional array of receivers configured so that at least one or more of the receivers in the array receive the optical beam notwithstanding of movement of the optical source due to patient motion.

* * * * *

UNITED STATES PATENT AND TRADEMARK OFFICE
CERTIFICATE OF CORRECTION

PATENT NO. : 7,173,426 B1  Page 1 of 1
APPLICATION NO. : 11/288555
DATED : February 6, 2007
INVENTOR(S) : Selaka Bandara Bulumulla and Glenn Alan Forman It is certified that error appears in the above-identified patent and that said Letters Patent is hereby corrected as shown below:

Col. 6, lines 16-26 Claim 7, should depend from Claim 2.

Col. 6, lines 32-42 Claim 9, should depend from Claim 2.

Col. 6, lines 43-54 Claim 10, should depend from Claim 2.

Signed and Sealed this

Eighth Day of September, 2009

David J. Kappos
*Director of the United States Patent and Trademark Office*